United States Patent [19]

Alchas et al.

[11] Patent Number: 5,372,945
[45] Date of Patent: Dec. 13, 1994

[54] DEVICE AND METHOD FOR COLLECTING AND PROCESSING FAT TISSUE AND PROCURING MICROVESSEL ENDOTHELIAL CELLS TO PRODUCE ENDOTHELIAL CELL PRODUCT

[76] Inventors: Paul G. Alchas, 29 Ponds Cir., Wayne, N.J. 07470; Alfred W. Prais, 245 Awosting Rd., Hewitt, N.J. 07421; Bruce E. Jarrell, 5700 N. Via Elena, Tucson, Ariz. 85718; Stuart K. Williams, 5181 N. Circulo Sobrio, Tucson, Ariz. 85718; Joseph A. DiPisa, Jr., 84 Maryann La., Wyckoff, N.J. 07481

[21] Appl. No.: 923,384

[22] Filed: Jul. 31, 1992

Related U.S. Application Data

[60] Continuation-in-part of Ser. No. 695,474, May 3, 1991, abandoned, and a continuation-in-part of Ser. No. 477,733, Feb. 9, 1990, abandoned, which is a continuation-in-part of Ser. No. 356,431, May 24, 1989, Pat. No. 5,035,708, which is a continuation-in-part of Ser. No. 244,496, Sep. 12, 1988, abandoned, which is a division of Ser. No. 742,086, Jun. 6, 1985, Pat. No. 4,820,626.

[51] Int. Cl.$^5$ .......................... C12S 3/00; C12M 1/40
[52] U.S. Cl. ........................ 435/267; 435/271; 435/288; 435/311; 422/101; 494/27; 494/30; 494/36
[58] Field of Search .................. 435/1, 240.21, 262, 435/267, 271, 284, 286, 287, 288, 296, 311, 316, 803; 422/72, 101-103, 113; 210/632, 360.1, 380.1, 406, 472; 209/12, 19; 494/16, 27, 30, 36; 604/35, 190, 406; 128/749

[56] References Cited

U.S. PATENT DOCUMENTS

| | | | |
|---|---|---|---|
| 2,184,152 | 12/1939 | Saffir | 604/403 |
| 2,533,149 | 12/1950 | Stang, Jr. | 23/1 |
| 2,910,406 | 10/1959 | Novak | 167/74 |
| 3,468,474 | 7/1969 | Shoblom et al. | 494/16 |
| 3,469,369 | 9/1969 | Helmke | 55/46 |
| 3,583,627 | 6/1971 | Wilson | 494/36 |
| 3,849,072 | 11/1974 | Ayres | 494/16 |
| 4,410,630 | 10/1983 | Zierdt | 435/284 |
| 4,416,778 | 11/1983 | Rogers | 494/16 |

(List continued on next page.)

FOREIGN PATENT DOCUMENTS

A049341  4/1982  European Pat. Off. .

(List continued on next page.)

OTHER PUBLICATIONS

Jarrell et al. "Human Endothelial Cell Growth in Culture" Journal of Vascular Surgery, vol. 1, No. 6, pp. 757-764 Nov., 1984.

(List continued on next page.)

*Primary Examiner*—William H. Beisner
*Attorney, Agent, or Firm*—Woodcock Washburn Kurtz Mackiewicz & Norris

[57] ABSTRACT

Methods and apparatus for collecting and processing tissue to produce an endothelial cell product having a vessel for rinsing, draining, digesting and isolating tissue. The vessel has a rinsing and digesting chamber for containing tissue during processing. An inlet in the rinsing and digesting chamber allows entry of rinsing solution and tissue from a liposuction device. A waste chamber in fluid communication with the rinsing and digesting chamber preferably connects with a vacuum source. An isolation chamber is separated from the rinsing and digesting chamber by a screen. An ampule in fluid communication with the isolation chamber includes a pair of ports controlled by valve devices to be selectively in fluid communication with the isolation chamber. After processing, the ampule isolates a pellet of endothelial cells and the valve devices permit the pellet to be in fluid communication with the ports. The method includes providing the vessel, introducing tissue to be processed, orienting the vessel to screen the tissue, introducing an enzyme and agitating to digest the tissue, centrifuging the vessel to transfer the cells from the digested tissue, and isolating the cells for retrieval.

12 Claims, 10 Drawing Sheets

U.S. PATENT DOCUMENTS

| | | | |
|---|---|---|---|
| 4,636,473 | 1/1987 | Kleinstreuer | 435/289 |
| 4,617,009 | 10/1988 | Ohlin et al. | 604/410 |
| 4,820,626 | 4/1989 | Saeki et al. | 430/596 |
| 4,820,626 | 4/1989 | Williams | 435/1 |
| 4,833,083 | 5/1989 | Saxena | 435/240.24 |
| 4,981,596 | 1/1991 | Shiino et al. | 210/650 |
| 5,035,708 | 7/1991 | Alchas et al. | 623/1 |

FOREIGN PATENT DOCUMENTS

| | | |
|---|---|---|
| 0080956 | 6/1983 | European Pat. Off. |
| 0264191 | 4/1988 | European Pat. Off. |
| 0265176 | 4/1988 | European Pat. Off. |
| 0320441 | 6/1989 | European Pat. Off. |
| A593676 | 12/1977 | Switzerland . |
| 1356794 | 6/1974 | United Kingdom . |
| 8303536 | 10/1983 | WIPO . |

OTHER PUBLICATIONS

Herring et al. "A Single and Staged Technique for Seeding Vascular Grafts with Autogenous Endothelium" Surgery, 1978 84:498–504.

Graham et al. "Cultured Autogenous Endothelial Cell Seeding of Vascular Prosthetic Grafts" Surg Forum 30:204–206 (1979).

Graham et al. "Expanded Polytetrafluoroethylene Vascular Prostheses Seeded with Enzymatically Derived and Cultured Canine Endothelial Cells" Surgery 91:550–559 (1982).

Dilley et al. "Endothelial Seeding of Vascular Prostheses" Jaffe ed. Biology of Endothelial Cells, the Hague: Martinus Nijhoff, 1984 pp. 401–411.

Berger et al. "Healing of Arterial Prostheses in Man It's Completeness" Ann. Surg 175:118–127 (1972).

Jaffe et al. "Synthesis of Antihemophilia Factor Antigen by Cultured Human Endothelial Cells" J. Clin. Invest. 55:2757–2764 (1973).

Lewis "Endothelium in Tissue Culter" Am. J. Anat. 30:39–59 (1922).

Jaffe et al. "Culture of Human Endothelial Cells Derived from Umbilical Veins" J. Clin. Invest. 52:2745–2756 (1973).

Glassberg et al. "Cultured Endothelial Cells Derived From Human Iliac Arteries" In Virtro 18:859–866 (1982).

Sharefkin et al. "Early Normilzation of Platelet Survival by Endothelial Seeding of Dacron Arterial Prostheses in Dogs" Surgery 92:385–393 (1982).

Stanely et al. "Enhanced Patency of Small Diameter Externally Supported Dacron Iliofemoral Grafts Seeded with Endothelial Cells" Surgery 92:994–1005 (1982).

Watkins et al. "Adult Human Saphenous Vein Endothelial Seeding of Vascular Prosthese" J. Surg. Res. 36:588–596 (1984).

Fishman "Endothelium: A Distributed Organ of Diverse Capabilities" Annals of New York Academy of Sciences, pp. 1–8 (1982).

Sauvage et al. "Interspecies Healing of Porous Arterial Prostheses" Arch Surg. 109:698–705 (1974).

F. Hess et al. "The Endothelialization Process of a Fibrous Polyurethane Microvascular prostheses After Implantation In The Abdominal Aorta of the Rat" Journal of Cardiovascular Surgery, vol. 24, No. 5, pp. 516–524 (Sep.–Oct. 1983).

W. K. Nicholas et al. "Increased Adherence for Vascular Endothelial Cells to Biomer Precoated With Extracellular Matrix" Trans. Am. Soc, Artif. Intern. Organs 28:208–212 (1981).

C. L. Ives et al. "The Importance for Cell Origin and Substrate in the Kinetics of Endothelial Cell Alignment in Response to Steady Flow" Trans. Am. Soc, Artif Intern. Organs 29:269–274 (1983).

S. G. Eskin et al. "Behavior of Endothelial Cells Cultured on Silastic and Dacron Velour Under Flow Conditions In Vitro Implications for Prelining Vascular Grafts with Cells" Artificial Organs 7(1):31–37 (1983).

T. A. Belden et al. "Endothelial Cell Seeding of Small-Diameter Vascular Grafts" Trans. Am. Soc. Artif. Intern. Organs 28:173–177 (1982).

W. E. Burkel et al. "Fate of Knitted Dacron Velour Vascular Grafts Seeded With Enzymatically Derived Autologous Canine Endothelium" Trans. Am. Soc. Artif. Intern. Organs 2:178–182 (1982).

Herring et al. "Seeding Arterial Prostheses With Vascular Endothelium" Ann. Surg. vol. 190, No. 1, pp. 84–90 (Jul. 1979).

A. Wesolow "The Healing of Arterial Prostheses: The State of the Art" Thorac. Cardiovasc. Surgeon 30:196–208 (1982).

T. Ishihara et al. "Occurrence and Significance of Endethelial Cells in Implanted Procine Bioprosthetic Valves" American Journal of Cardiology 48:443–454 (Sep. 1981).

Williams et al. "Micropinocytic Ingestion of Glycosylated Albumin by Isolated Microvessels: Possible Role in Pathogenesis of Diabetic Microangiopathy" Proc. Natl. Acad. Sci. USA vol. 78, No. 4, pp. 2393–2397 (Apr. 1981).

Williams et al. "Regulation of Micropinocytosis in Capillary Endothelium by Multivalent Cations" Microvascular Research 21 175–182 (1981).

Williams et al. "Quantitative Determination of Deoxyribonuclein Deoxyribonuclein Acid from Cells Collected on Filters" Analytical Biochemistry 107:17–20 (1980).

Wagner et al. "Exclusion of Albumin from Vesicular Ingestion by Isolated Microvessels" Microvascular Research 19:127–130 (1980).

(List continued on next page.)

Williams et al. "Metabolic Studies on the Micropinocytic Process in Endothelial Cells" Microvascular Research 18:175-184 (1979).

Williams "Vesicular Transport of Proteins by Capillary Endothelium" Annals of the New York Academy of Sciences 457-467 (1983).

Williams et al. "Enhanced Vesicular Ingestion of Nonenzymatically Glucosylated Proteins by Capillary Endothelium" Microvascular Research 28:311-321 (1984).

Williams et al. "Endocytosis and Exocytosis of Protein in Capillary Endothelium" Journal of Cellular Physiology 120:157-162 (1984).

Williams et al. "Isolation and Characterization of Brain Endothelial Cells: Morphology and Enzyme Activity" Journal of Neurochemistry 35: 374-381 (Aug. 1980).

McDonagh et al. "The Preparation and Use of Fluorescent-Protein Conjugates for Microvascular Research" Microvascular Research 27:14-27 (1984).

Madri et al. "Capillary Endothelial Cell Cultures: Phenotypic Modulation by Matrix Components" Journal of Cell Biology vol. 97 (Jul. 1983) pp. 153-165.

Williams et al. "Adult Human Endothelial Cell Compatibility With Prosthetic Graft Material" Journal of Surgical Research 38:618-629 (1985).

Kern et al. "Isolation and Culture of Microvascular Endothelium from Human Adipose Tissue" J. Clin. Invest. 71:1822-1829 (Jun. 1983).

Van Wachem et al. "Interaction of Cultured Human Endothelial Cells with Polymeric Surfaces of Different Wettabilities" Bimaterials 6:403-408 (1985).

Azizkham et al. "Mast Cell Heparin Stimulates Migration of Capillary Endothelial Cells in Vitro" J. Exp. Med. vol. 152 Oct. (1980) pp. 931-944.

Roblin et al. "Cell Surface Changes Correlated with Density Dependent Growth Inhibition: Glycosaminoglycan Metabolism in 3T3, SV3T3, and Con A Selected Revertant Cells" Biochemistry vol. 14, No. 2 (1975) pp. 347-357.

Yang et al. "The Effect of Heparin on Growth of Mammalian Cells in Vitro" (40290) Proceedings of the Soc. for Experimental Biology and Medicine 159:88-93 (1978).

Thornton et al. "Human Endothelial Cells: Use of Heparin in Cloning and Long-Term Serial Cultivation" Science (11 Nov. 1983), vol. 222, pp. 623-625.

Laterra et al. "Functions for Fibronectin, Hyaluronate and Heparin Proteoglycans in Substratum Adhesion of Fibroblasts" Extracellular Matrix pp. 197-207, (1982).

Maciaq et al., "Factors Which Stimulate the Growth of Human Umbilical Vein Endothelial Cells in Vitro", Jaffe, E. A. (ed.) Biology of endothelial cells, (1984) Martinus Nijohff, pp. 87-140.

Madri, "The Immunochemistry of Extracellular Matrix", Boca Raton, Fla., CRC Press, (1982), vol. 1:75-90.

Baker et al., "Endothelialization of Human Collagen Surface with Human Adult Endothelial Cells", American Journal of Surgery, 150:197-200 (Aug., 1985).

Jarrell et al., "Use of Freshly Isolated Capillary Endothelial Cells for the Immediate Establishment of a Monolayer or a Vascular Graft at Surgery", Surgery vol. 100 (Aug. 1986) pp. 392-399.

Radomski et al., "Initial Adherence of Human Capillary Endothelial Cells to Dacron", Journal of Surgical Research, vol. 42 (1987) pp. 133-140.

Berger et al. "Healing of Arterial Prostheses in Man: It's Incompleteness", Ann. Surg. 175: 118-127 (1972).

Abedin, M. Z. et al. "Collagen Heterogeneity and Its Functional Significance" Die Angewandte Markromolekulare Chemie, vol. 111, No. 1701 Jan. (1983), pp. 107-222.

DEVICE AND METHOD FOR COLLECTING AND PROCESSING FAT TISSUE AND PROCURING MICROVESSEL ENDOTHELIAL CELLS TO PRODUCE ENDOTHELIAL CELL PRODUCT

CROSS-REFERENCE TO RELATED APPLICATIONS

This application is a continuation-in-part of application Ser. No. 477,733, filed Feb. 9, 1990 entitled "Device for Processing Fat Tissue to Produce Endothelial Cell Product", now abandoned which is a continuation-in-part of application Ser. No. 356,431, filed May 24, 1989 entitled "Endothelial Cell Procurement and Deposition Kit", and issued Jul. 30, 1991 as U.S. Pat. No. 5,035,708, which is a continuation-in-part of application Ser. No. 244,496, filed Sep. 12, 1988 entitled "A Method of Treating a Synthetic or Naturally Occurring Surface with Microvascular Endothelial Cells and the Treated Surface Itself", now abandoned which is a division of application Ser. No. 742,086, filed Jun. 6, 1985 and issued Apr. 11, 1989 as U.S. Pat. No. 4,820,626 entitled "Method of Treating a Synthetic or Naturally Occurring Surface with Microvascular Endothelial Cells, and the Treated Surface Itself," each of which prior applications is assigned in whole or in part to Thomas Jefferson University, which is a co-assignee with Becton Dickinson and Company of the present application, which applications are hereby incorporated by reference.

This application is also a continuation-in-part of application Ser. No. 695,474, filed May 3, 1991 entitled "Device and Method for Collecting and Processing Fat Tissue and Procuring Microvessel Endothelial Cells", now abandoned.

This application is related to applications Ser. No. 927,745, filed Nov. 6, 1986 entitled "Method of Determining Endothelial Cell Coverage of a Prosthetic Surface", now abandoned; Ser. No. 848,453, filed Apr. 4, 1986 entitled "A Method of Treating a Synthetic or Naturally Occurring Surface with Collagen Laminate to Support Microvascular Endothelial Cell Growth and the Surface Itself", now abandoned; Ser. No. 114,242, filed Oct. 28, 1987 entitled "Method of Reendothelializing Vascular Linings" issued as U.S. Pat. No. 4,883,755 on Nov. 28, 1989, all of which are continuations-in-part of parent application Ser. No. 742,086, filed Jun. 6, 1985 and issued Apr. 11, 1989 as U.S. Pat. No. 4,820,626, each of which applications is assigned to Thomas Jefferson University, all of which applications are hereby incorporated by reference.

BACKGROUND OF THE INVENTION

While an autologous vein remains the graft of choice, advanced vascular disease and prior surgical intervention limit the availability of autologous grafts. Therefore, the use of synthetic grafts provides a means for restoring blood flow to ischemic areas when no alternative is available. Over the past three decades, artificial grafts have been used to provide immediate restoration of blood flow to areas of ischemia as a result of atherosclerotic vascular disease. In addition, they have been used to provide vascular access for hemodialysis in patients with chronic renal failure, and in the repair of arterial aneurysms.

Although initially successful in restoring perfusion to ischemic tissues, the long term prognosis for these grafts is not encouraging. Commercially available grafts are far from ideal due to their inherent thrombogenicity. Over an extended period of time, grafts less than 4 mm in diameter lose their patency as they become occluded via fibrin deposition and cellular adhesion. This process appears to be secondary, and to be due in part to the thrombogenic nature of the nude, i.e. non-endothelialized, surface of an implanted prosthesis. See Berger et al., "Healing of Arterial Prostheses in Man: Its Incompleteness", Ann. Surg. 175:118-27 (1972).

Thus, much current research is being focused on lining prostheses with human endothelial cells, for producing a non-thrombogenic endothelial cell surface such as exists in native human vessels. In dogs, seeding of endothelial cells onto both small and large diameter grafts has been shown to result in a complete endothelial cell lining in one to four months. Since vascular endothelium is said to represent a unique non-thrombogenic surface, endothelial cells are reported to be "the first logical choice for lining small diameter vascular grafts." The transplantation of a functional endothelial cell lining onto the surface of a vascular graft has proven to increase patency rates and decrease thrombus formation on the flow surface in animal models.

Past and present studies have focused on the isolation of large vessel endothelial cells from vein segments, with the subsequent seeding of these cells on the graft lumenal surface. Tissue culture advances have also made the generation of large numbers of endothelial cells for high-density seeding on vascular prosthesis possible. These techniques have major drawbacks in the clinical setting. Endothelialization occurs at a slow rate, when low density seeding techniques are applied. High-density seeding, using cultured endothelial cells, requires the use of undefined media not easily applicable to the clinical setting.

It has been recognized that human microvascular endothelial cells i.e. the cells which are derived from capillaries, arterioles, and venule, will function suitably in place of large vessel cells even though there are morphological and functional differences between large vessel endothelial cells and microvessel endothelial cells in their native tissues. Microvascular endothelial cells are present in an abundant supply in body tissue, most notably in fat tissue, and may be used to establish a degree of implantation confluence prior to implantation, i.e. at least 50°, which dramatically improves the prognosis of most implants. For purposes of further description, fat tissue is designated as the exemplary source of microvascular endothelial cells, but it is recognized that endothelial cells from other tissues may be used as well.

To overcome the problems associated with seeding large vessel endothelial cells on prosthetic grafts, methods were developed for the isolation of microvessel endothelial cells from autologous adipose tissue, followed by high density seeding of a vascular prosthesis.

Although microvessel endothelial cells have been shown to be capable of endothelializing a blood-contacting surface, methods of procuring and depositing these cells in an operating room setting present special considerations. A vascular graft or other implant is treated to confluence using microvascular endothelial cells which are separated from fat, which is obtained at the beginning of the same uninterrupted surgical procedure. Fat tissue is removed from the patient after sterile conditions have been established. Microvascular endothelial cells in that fat area are then quickly separated from their related tissue by enzymatic digestion and centrifugation, and are used to treat a surface which is then implanted in the patient during the latter stages of the same operation. This procedure permits a patient to receive a graft which has been treated up to or above confluence with his own fresh endothelial cells.

The microvascular rich tissue obtained is perinephric fat, subcutaneous fat, omentum, or fat associated with the thoracic or peritoneal cavity. This tissue is then subjected to digestion using a proteolytic enzyme such as collagenase, comprising caseanase and trypsin, which is incubated with the tissue until the tissue mass disperses to produce a tissue digest. The microvascular endothelial cells are then separated from the digest using low speed centrifugation to produce an endothelial cell rich pellet. The pellet is washed with a buffered saline solution.

The resulting microvascular endothelial cells are then, preferably, suspended in buffered saline solution containing plasma protein, preferably about 1% plasma protein. This suspension, which comprises, on a volumetric basis, a pellet to solution ratio of 1:5 to 1:15, or preferably about 1:10, is then used to treat the surface by incubating cells with that surface until sufficient adherence of the microvascular endothelial cells to that surface occurs to provide at least 50° confluence. As a result, an improved graft implant is provided having endothelialized surfaces which are either confluent, or which reach confluence quite rapidly (doubling within one population) following implantation.

Implants which can be treated to produce such an endothelial cell lining include but are not limited to, for example, intravascular devices such as artificial vascular prostheses, artificial hearts, and heart valves. The kit and methods of this invention for endothelializing surfaces can be used for surfaces comprised of known synthetic materials such as polyester, polytetrafluoroethylene (PTFE), or naturally occurring materials, such as umbilical vein, saphenous vein, and native bovine artery.

Methods currently used employ standard laboratory equipment such as beakers, flasks, centrifuge tubes, shaker baths, pipettes, syringes, and sterile hoods. In one method the donated tissue is immediately transferred to ice cold buffered saline (pH 7.4) wherein the buffering agent is preferably a phosphate, i.e. a phosphate buffered saline (PBS). The tissue is minced with fine scissors and the buffer decanted. The proteolytic enzyme collagenase, containing caseanase and trypsin, is added to the tissue and incubated at 37° C. until the tissue mass disperses. The digestion occurs within 30 minutes and generally should be less than 20 minutes. The digest is transferred to a sterile test tube and centrifuged at low speed (700×g) in a table top centrifuge for 5 minutes at room temperature.

The pellet of cells thus formed consists of greater than 95% endothelial cells. These endothelial cells are described herein as microvascular endothelial cells (MEC) since they originate from the arterioles, capillaries and venule, all elements of the microvasculature. The MEC pellet is washed 1 time by centrifugation with buffered saline, preferably PBS. The MEC suspension is then, preferably, pelletized by centrifugation (200×g) and the pellet resuspended with protein containing buffer solution. Resuspension should be performed at a ratio of approximately 1:5 to 1:15 or about 1:10 volumes of packed microvascular endothelial cells to buffer solution. The cell suspension is added to tubular grafts and the ends clamped, or the cells layered upon the surface to be treated.

Optimum periods for cell interaction vary upon the material of the prosthesis, the nature of any pretreatments it may have received, and whether the surface of the prosthesis has been modified to improve its acceptance of the MEC. Following incubation for a sufficient time to permit adherence of the endothelial cells with the prosthesis surface, the surface is washed with a protein containing buffer.

In U.S. Pat. No. 4,820,626, and related applications, methods of treating a graft surface with endothelial cells are disclosed. According to those methods, subcutaneous adipose tissue is aspirated via a cannula and transferred by vacuum into a mucous trap. The trap is then transferred to a sieve inside a funnel which is placed in a sterile beaker. A rinsing solution is then poured over the tissue to remove red blood cells and lysed fat. The tissue is manually poured into a sterile Erlenmeyer flask containing collagenase solution and agitated at 370° C. for 20 minutes. The collagenase slurry is manually poured into sterile conical centrifuge tubes, and spun for seven minutes at 700×g. The endothelial cells are then pipetted out of the tube. A graft is tied to a male luer extension, and secured within a tube. The cells are resuspended in serum protein media and drawn into a syringe using a needle and syringe. The cells are forced into the lumen of the graft. The graft is manually rotated for 2 hours.

In spite of these advances, a need still exists for a simple, reliable method for producing endothelial cell coatings on a graft in an operating room setting, and this invention solves that need. The present invention provides for the ready isolation of large quantities of endothelial cells which can be easily performed in an operating room. While endothelial cells can be isolated from tissues other than fat, such as brain, lung, retina, adrenal glands, liver and muscle, the use of fat tissue as the source of the cells is preferred due to its abundance and availability, and due to the fact that its removal should not adversely affect the patient being treated. Although less preferred, it is possible to obtain human perinephric fat from brain-dead but heart beating cadaver donors, or from donors other than the donor's surgery. The isolated endothelial cells are then deposited on a graft for implantation.

SUMMARY OF THE INVENTION

A device for collecting and processing tissue to produce an endothelial cell product is provided and includes a vessel for rinsing, draining, digesting and isolating tissue. The vessel has a rinsing and digesting chamber for containing tissue during processing. An inlet is in the rinsing and digesting chamber for connection in fluid communication with a liposuction means. A drain chamber or waste chamber is preferably provided in the vessel and is in fluid communication with the rinsing and digesting chamber. The waste chamber has a connection for fluid communication with a vacuum source. A screen is in the vessel for separating the rinsing and digesting chamber from the waste chamber to allow filtered transfer of rinsing solution from the rinsing and digesting chamber to the waste chamber.

An isolation chamber is in the vessel with the rinsing and digesting chamber and is separated from the rinsing and digesting chamber by another screen. A pair of ports are preferably separated by a channel that forms an ampule, each of which may be selectively attached in fluid communication with the ampule by a valve means. Rinsed, digested, and processed tissue, produced under sterile conditions, may be collected within the ampule as endothelial cell product. The vessel is generally cylindrical, having a frusto-conical end, to house the isolation chamber.

A preferred method of collecting and processing tissue to produce an endothelial cell product has the step of providing a collecting vessel for processing tissue to produce an endothelial cell product, the vessel having a rinsing and digesting chamber, a waste chamber and an isolation chamber. Another step is introducing tissue to be processed into the rinsing and digesting chamber. Another step is introducing rinsing solution into the rinsing and digesting chamber. A further step may be orienting the vessel to screen the tissue to be processed in the rinsing and digesting chamber from rinsing solution passed into the waste chamber. An additional step is introducing an enzyme into the rinsing and digesting chamber. This is followed by the steps of heating the tissue to be processed and the enzyme for a time period and at a temperature sufficient to digest, while agitating the rinsing and digesting chamber to digest the tissue with the enzyme. Centrifuging the vessel transfers the cells from the rinsing and digesting chamber into the isolation chamber. As a further step, the pellet of microvessel endothelial cells is isolated by selective operation of a valve means.

DETAILED DESCRIPTION OF THE INVENTION

In accordance with the preferred methods useful with the present invention, subcutaneous fat is removed from a patient using modified liposuction techniques and transferred to a self-contained, closed device where the fat can be stored under sterile conditions until needed. The fat is sterilely transferred to a digestion device where it is initially washed to remove red blood cells and other debris, followed by a controlled collagenase digestion for about 20 minutes at about 37° C. The fat slurry is then transferred to an endothelial cell isolation device, again under sterile conditions, where endothelial cells sediment into an isolation device, allowing automatic retrieval of the isolated endothelial cells. The cell suspension is then sterilely transferred to a processing unit wherein the cells are rapidly filtered onto the graft surface under sterile conditions. The endothelial cell isolation and deposition process requires only about 40 minutes for completion using the apparatus described herein. Following an incubation period, the graft is ready for implantation into the patient. In paired comparisons between the present invention and the methods practiced previously, equivalence and reproducibility in the number of isolated endothelial cells and adherence of the cells to graft surface have been observed. The system yields endothelial cell product in numbers acceptable for subsequent high density seeding, e.g., in a range of about $5.14 \times 10^6$ to $4.24 \times 10^7$ cells from 50 cc of fat, and adherence to the graft surface. The apparatus of the present invention deposits cells along the entire length and diameter of the graft consistently, with no significant difference in cell concentration as compared by analysis of variance. Significant advantages of the technique to which the present invention is preferably applied are: 1) closed, sterile fluid path; 2) minimal user input; 3) compatibility with an operating room environment; and 4) optimization of the conditions to a highly reproducible process from patient to patient.

Figure 7:
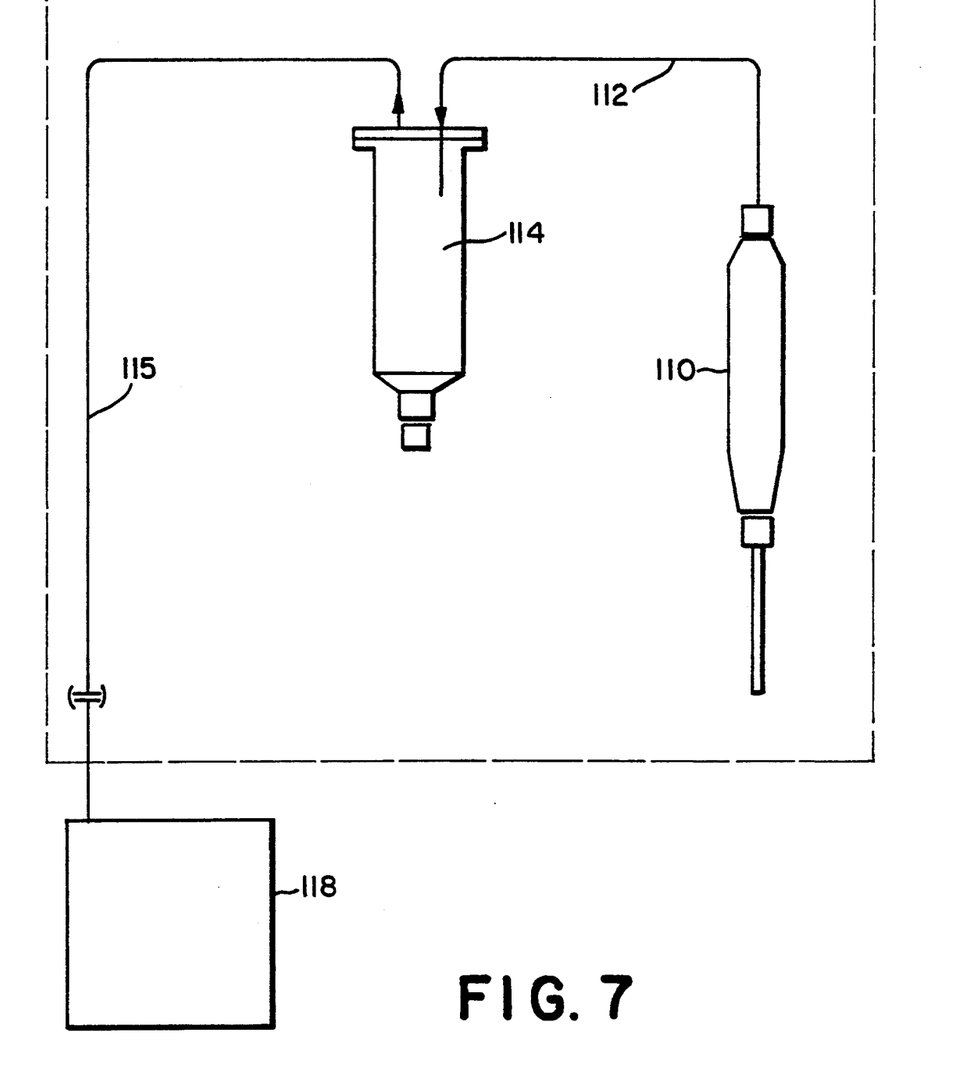
FIG. 7 is a schematic of an embodiment of apparatus useful with the present invention.

Generally, a system wherein the present invention is useful comprises of five primary subsystems: 1) fat collection unit; 2) digestion unit; 3) endothelial cell isolation unit; 4) vascular graft processing unit; endothelial cell deposition unit. The fat collection unit collects subcutaneous fat tissue sample from a patient. A schematic of a fat collection unit which is used to collect fat containing microvascular endothelial cells from a patient to receive a graft, which fat is ultimately collected into a fat collection device, is illustrated in FIG. 7. The components include: in-flow tubing 112, fat collection device 114, vacuum tubing 115, aspiration cannula 110 and an aspiration pump 118. The aspiration pump 118 is used to suction subcutaneous fat tissue from the patient through the cannula 110 and in-flow tubing 112 and into the fat collection device 114.

Figure 1:
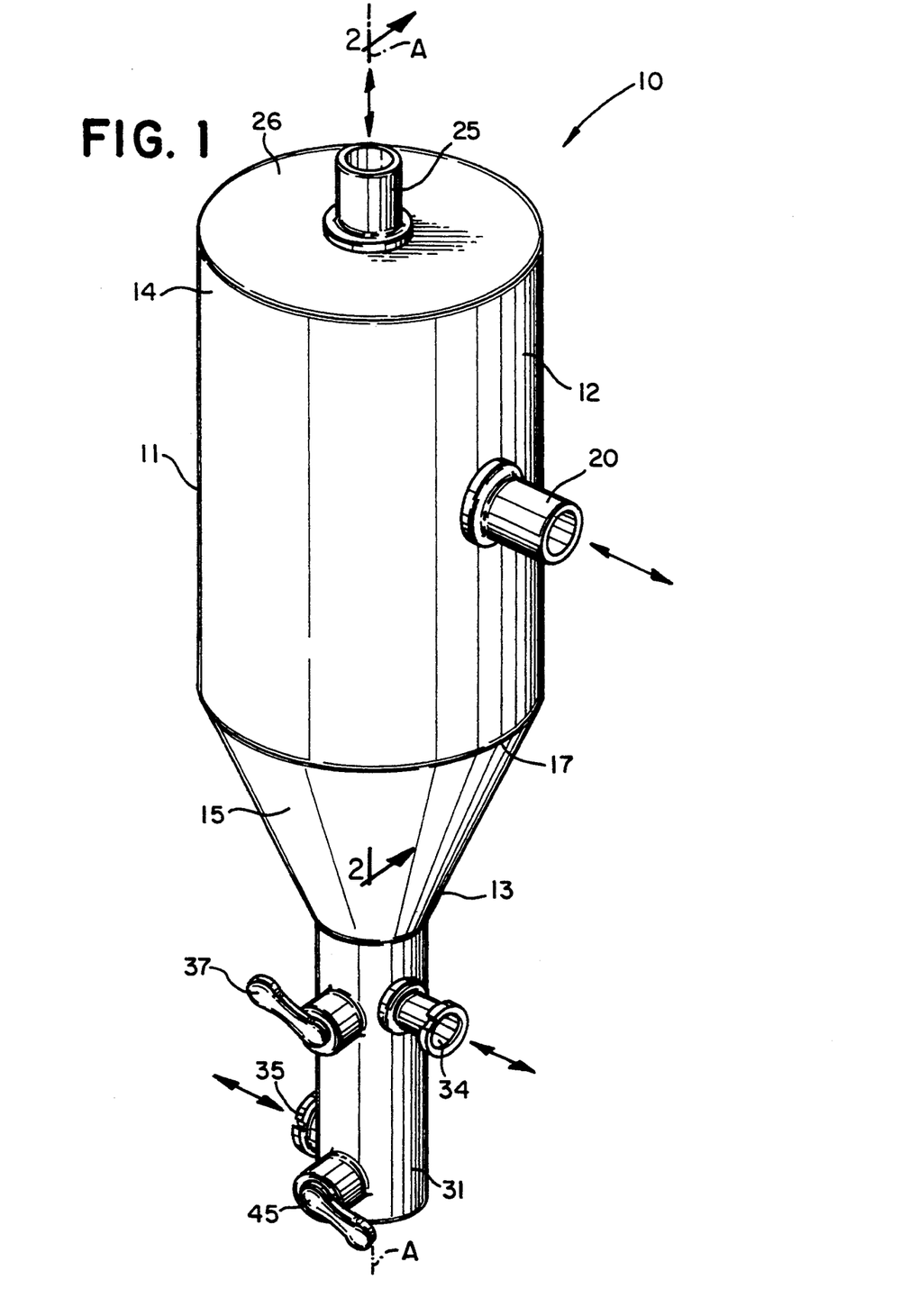
FIG. 1 is a perspective view of a device for collecting and processing tissue to produce an endothelial cell product.

Referring now to FIG. 1 there is shown generally an embodiment of the device 10 of the present invention for collecting and processing tissue to produce an endothelial cell product. In accordance with certain aspects of the present invention, the fat collection and processing functions described above are performed in a single unit as shown. A vessel 11 is used for rinsing, draining, digesting and isolating tissue for the device 10. As shown in the side elevational views of FIGS. 2-5, the vessel 11 is comprised of two parts 12,13. While not required, the vessel 11 is most preferably made of a low cost polymer that is easy to shape and resistant to the substances that will be handled during processing endothelial cells. In a preferred embodiment the upper part 12 is an inverted cup 14, and the lower part 13 is a frusto-conical funnel 15 with a top edge 16 that conjugates with an open bottom 17 of the inverted cup 14 to form an enclosure 18 in the vessel 11. A rinsing and digesting chamber 19 is defined within this enclosure 18. The rinsing and digesting chamber 19 is contained within the inverted cup 14 of the vessel 11 so that tissue can be suitably handled during processing. An inlet 20 is provided in side 21 of the rinsing and digesting chamber 19 for connection in fluid communication with an external liposuction means such as the cannula 110 shown in FIG. 7, for introducing tissue having microvessel endothelial cells into the rinsing and digesting chamber 19.

Figure 2:
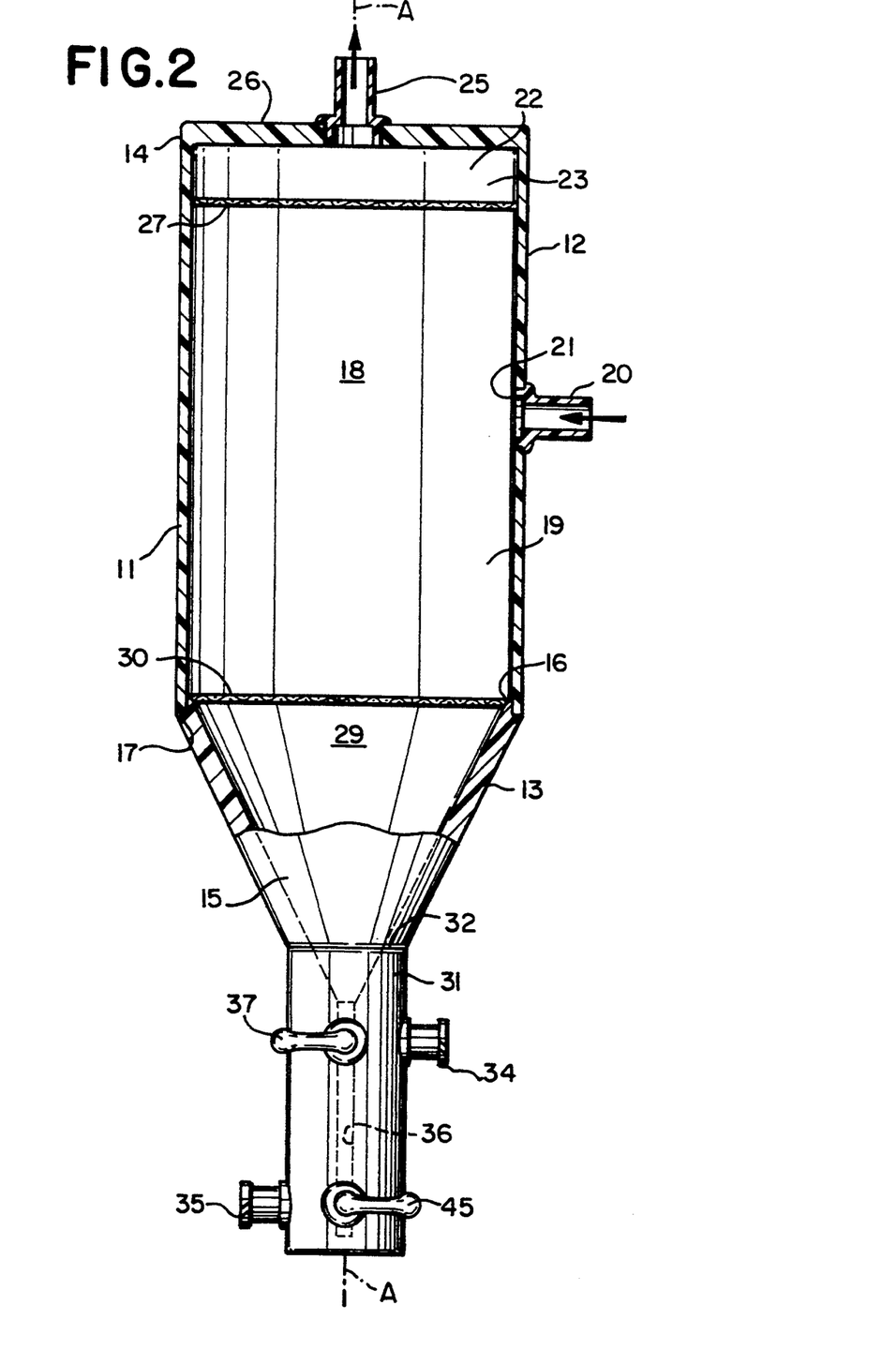
FIG. 2 is a partial sectional view of the device of FIG. 1 taken along lines 2—2 of FIG. 1, and showing the valve handles in a first position during centrifugation.
Figure 4:
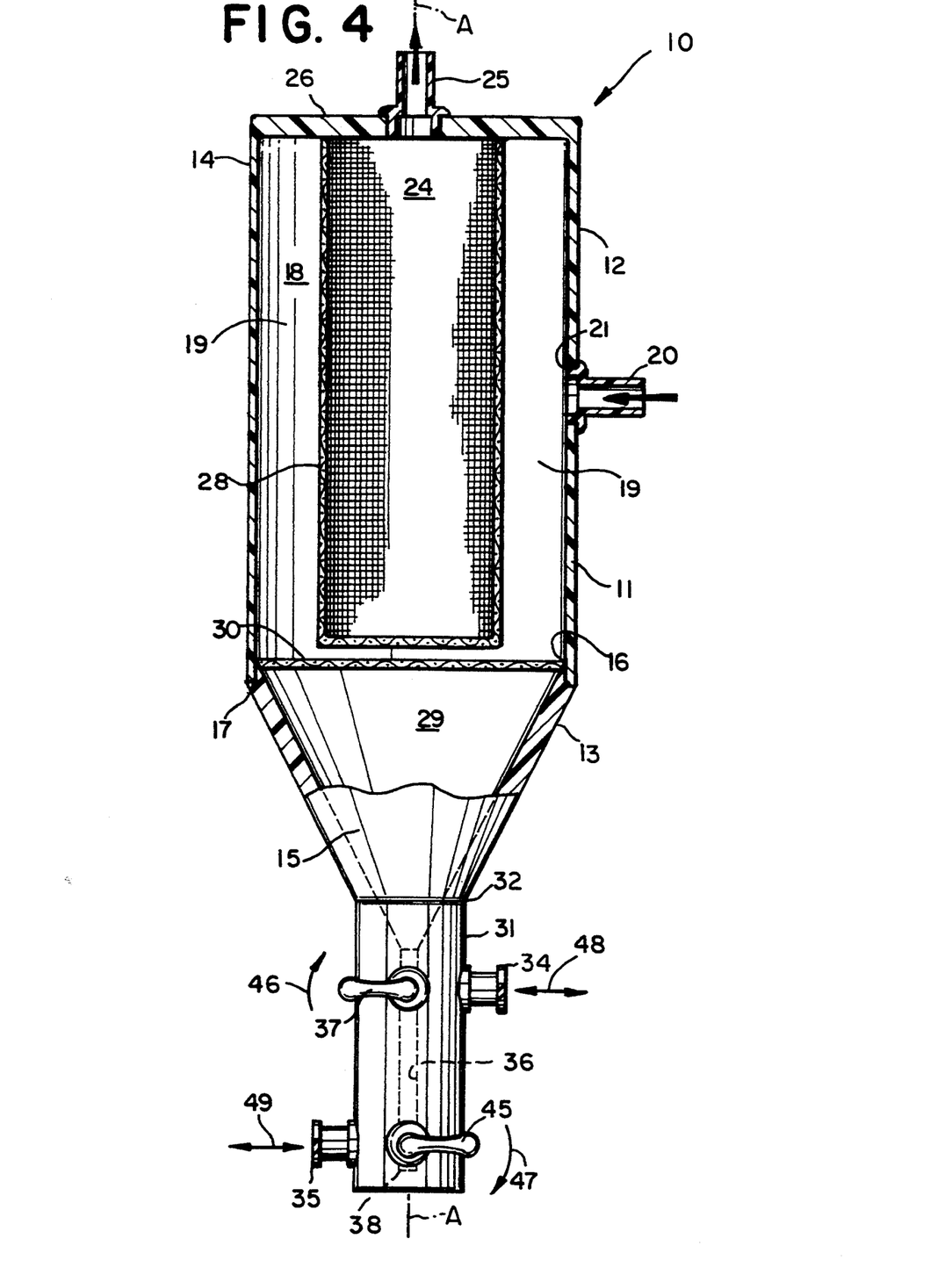
FIG. 4 is a side elevational view, partially in section, showing a device similar to that of FIGS. 1-3, but with a modified filter arrangement illustrating the invention.
Figure 5:
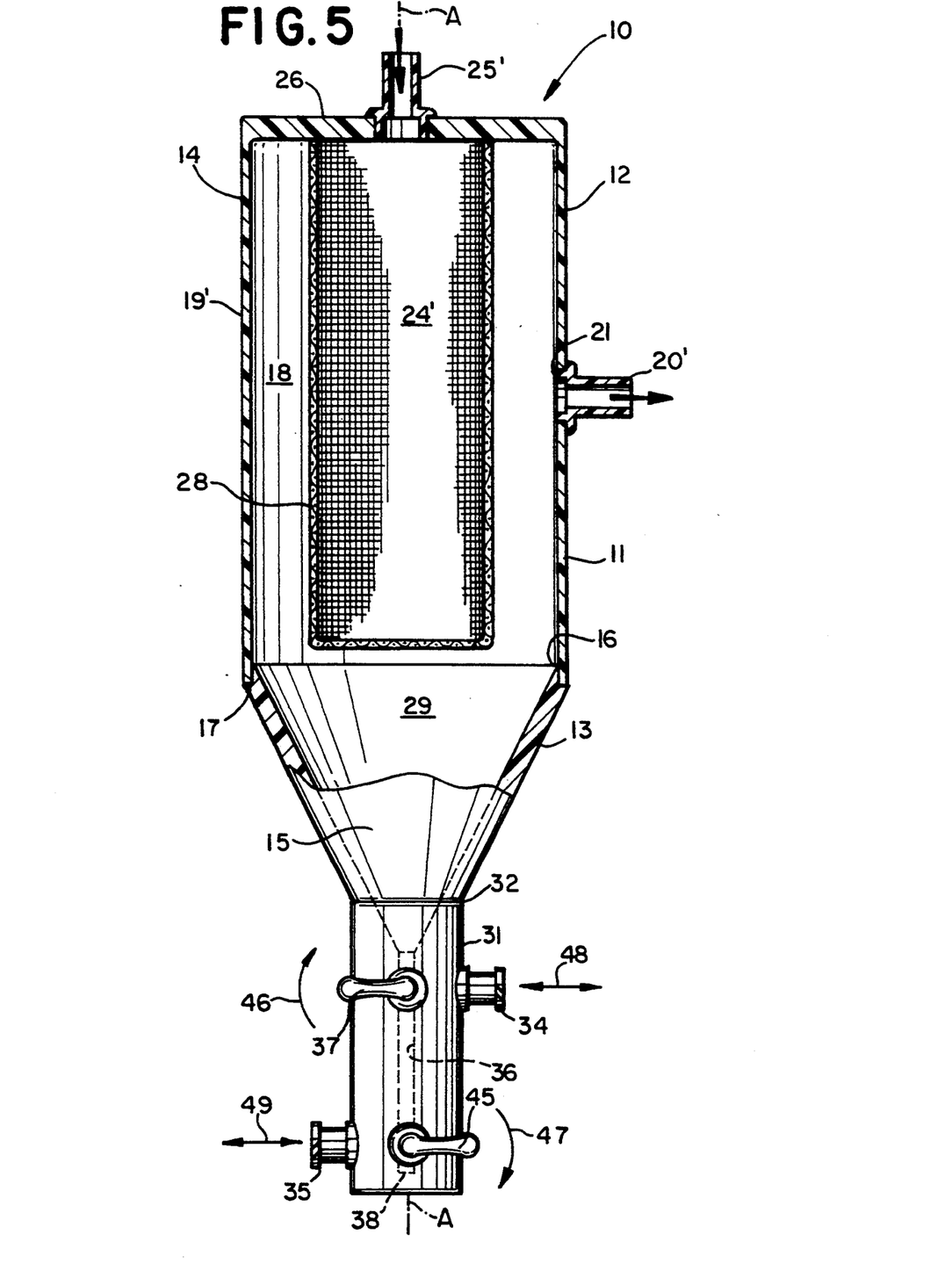
FIG. 5 is a side elevational view, partially in section, showing a modification of the device of FIG. 4 and further illustrating the invention.

As shown in FIG. 2, a drain chamber or waste chamber 22 is located within an upper inside portion 23 of the inverted cup 14 of the vessel 11 and is in fluid communication with the rinsing and digesting chamber 19. In FIG. 4, an alternate drain chamber or waste chamber 24 is illustrated that is centrally located within enclosure 18. Both waste chambers 22,24 have a connection 25 located to pass through a top 26 of the inverted cup 14 for allowing fluid communication with a vacuum source. In FIG. 5, a device similar to that of FIGS. 2–4 is shown, but the connections of 20 and 25 are reversed. Specifically, the inlet in FIG. 5 is 25' and the outlet connection is 20'; the waste chamber is thus now 19' and the rinsing and digesting chamber is 24'. The rinsing and digesting chamber 24' is centrally located within enclosure 18.

In FIG. 2, an upper screen 27 positioned within the vessel 11, inside inverted cup 14, separates the rinsing and digesting chamber 19 from the waste chamber 22 to allow filtered transfer of rinsing solution from the rinsing and digesting chamber 19 to the waste chamber 22. The screen 27 may be of various configurations and as shown in FIG. 2, the screen 27 is preferably flat. As a result, the waste chamber 22 is adjacent to upper inside portion 23 of the inverted cup 14, and the rinsing and digesting chamber 19 is immediately beneath. In FIG. 4 the screen 28 is shown in the shape of a cylinder, which defines the waste chamber 24 within the center of the inverted cup 14 along an axis "A" thereof. The rinsing and digesting chamber 19 circumscribes or fits about the screened in waste chamber 24 in a surrounding fashion.

Lower part 13 defines a frusto-conical funnel 15 with an internal chamber 29 and having a top edge 16 which is connected to the open bottom 17 of inverted cup 14 to form a combined enclosure 18,29. Referring to the embodiments of FIGS. 2–4, each preferably has a flat transverse screen 30 that is positioned adjacent top edge 16 of funnel 15. It should be noted that the embodiment of FIG. 5 does not include such a screen 30. A tube 31 connects to the apex 32 of the funnel 15. The tube 31 carries a pair of spaced apart ports 34,35, connected to a vertical channel that forms an ampule 36, positioned centrally within the tube 31. Ports 34,35 are for selective communication with the ampule 36 that is accomplished by valves 37,45, respectively, as shown in FIG. 4. The valves 37,45 may be simple stopcocks as are commonly found in medical accessories. To achieve this, valve 37 is rotated as indicated by arrow 46, and valve 45 is rotated as indicated by arrow 47. Arrows 48, 49 show flow direction two ways through ports 34,35. Using valves 37,45 permits rinsed, digested and processed tissue produced under sterile conditions to be isolated within the ampule 36 as a microvessel endothelial cell pellet. To remove the pellet, the valves 37,45 are adjusted to allow the pellet to be drawn off through one of ports 34,35.

Figure 2A:
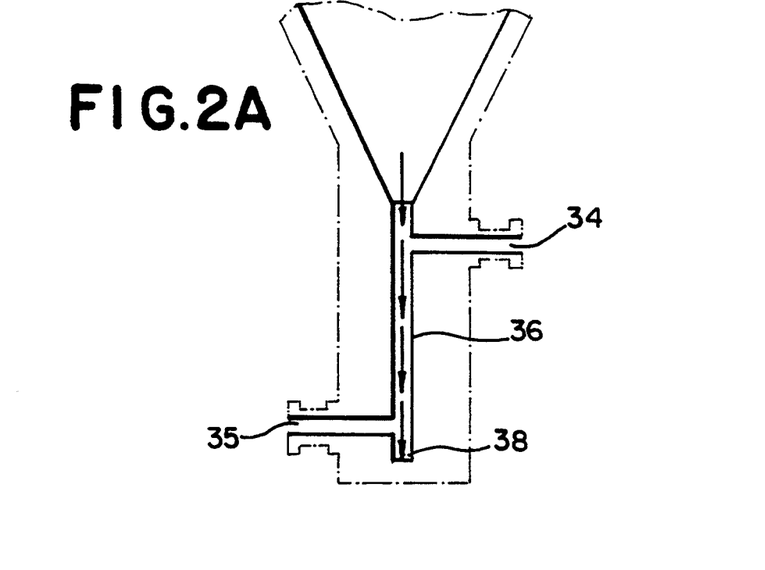
FIG. 2A is a schematic of the path of the flow through the valves and ports during centrifugation.
Figure 3:
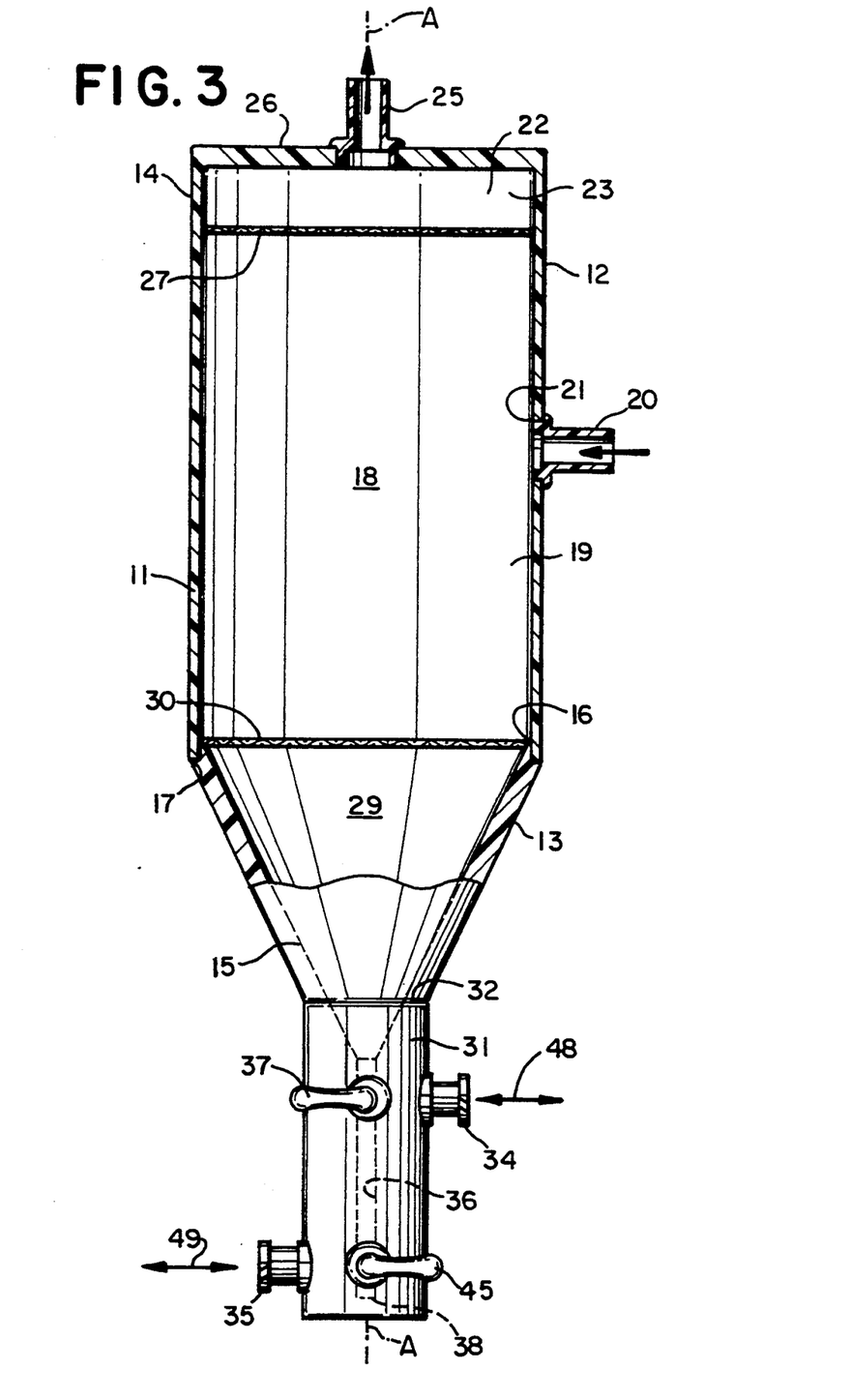
FIG. 3 is a partial sectional view of the device of FIG. 1 similar to that of FIG. 2, but with the valve handles in a second position after centrifugation.
Figure 3A:
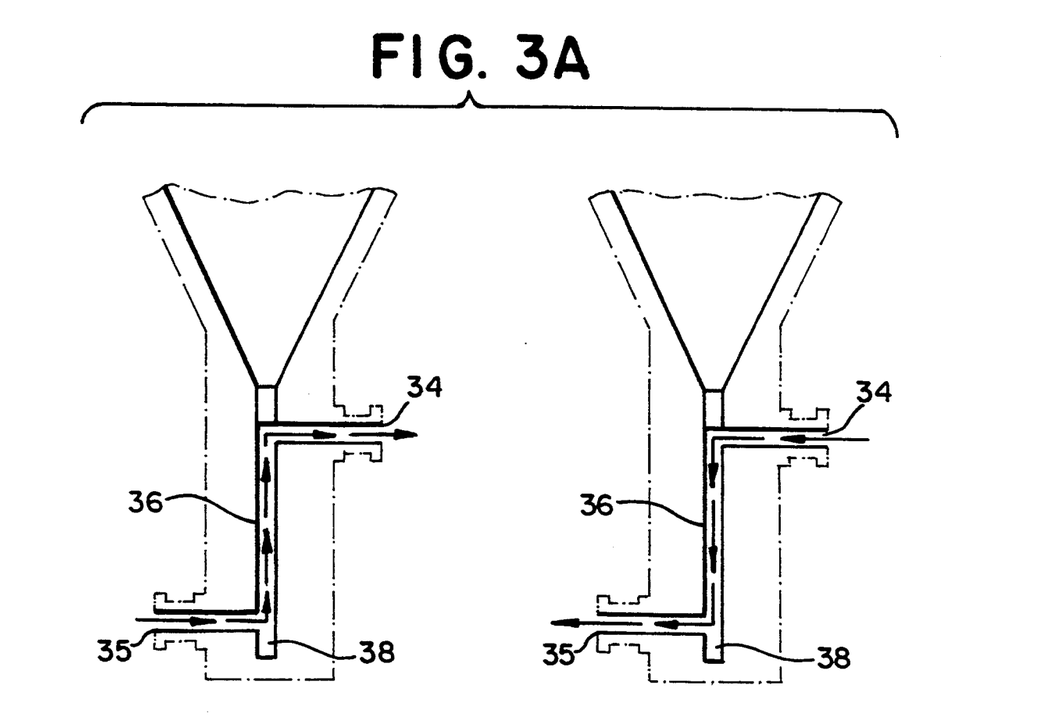
FIG. 3A is a schematic of the possible paths of the flow through the valves and ports after centrifugation.

FIG. 2A shows a schematic view of the flow path through the valves 37,45 during centrifugation. This flow path traps red blood cells in a trap 38 at the bottom of ampule 36, as shown in FIG. 2A. The trap 38 collects red blood cells during centrifugation because they are denser than the microvessel endothelial cells. After centrifugation, the valves 37, 45 can be adjusted as shown schematically in FIG. 3A. As shown, two flow paths are possible such that the isolated cells can be removed from ampule 36 and trap 38 by vacuum or pressure applied to either ports 34,35.

In another aspect of the present invention, a method of collecting and processing tissue to produce an endothelial cell product is also disclosed. The various steps in a preferred embodiment of this process are shown on the schematic diagram of FIG. 6. To perform the method, a vessel 11 for processing tissue to produce an endothelial cell product such as that described herein is provided. The vessel 11 preferably has a rinsing and digesting chamber 19, a waste chamber 22,24 and an isolation chamber 29.

Figure 6:
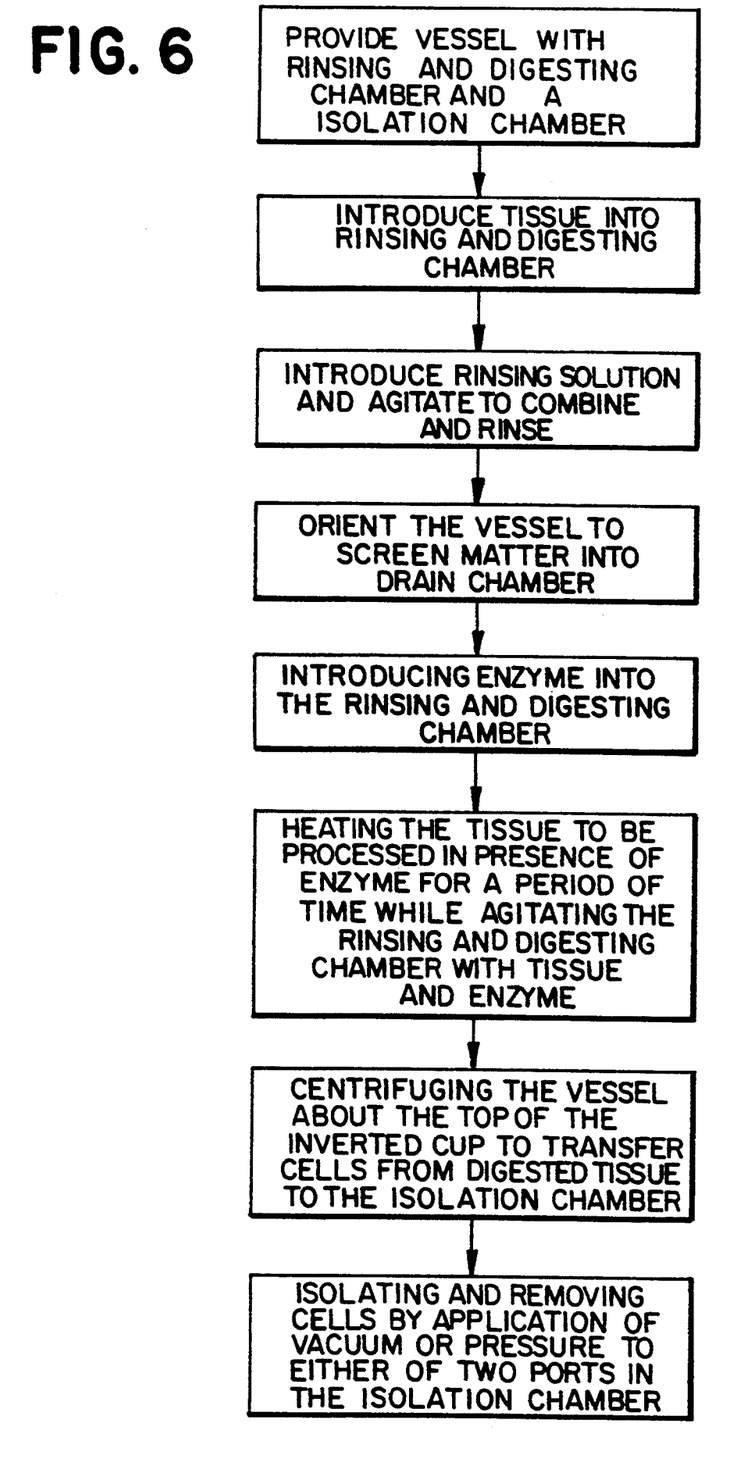
FIG. 6 is a flow diagram illustrating the steps in the process of collecting and processing tissue to produce an endothelial cell product.

Introducing tissue to be processed into the rinsing and digesting chamber 19 is a preliminary step of the processing method. The tissue may be obtained from a liposuction procedure. Orienting the vessel permits vacuum and gravity to filter off unneeded liquid from the tissue sample through a screen 30, which separates the tissue to be processed in the rinsing and digesting chamber 19 from rinsing solution which passes into the waste chamber 22,24. The method is continued by introducing an enzyme into the rinsing and digesting chamber 19, and heating the tissue to be processed in the presence of an enzyme for a period of time, and at a temperature sufficient to digest the tissue. The digestion is assisted by the step of agitating the rinsing and digesting chamber 19 containing the tissue and enzyme.

Centrifuging the vessel about the top 26 of the inverted cup 14 collects the cells from the digested tissue from the rinsing and digesting chamber 19 in the isolation chamber 29. Any red blood cells in the rinsed and digested tissue will be collected in the trap 38 at the bottom of ampule 36 because, as mentioned previously the red blood cells are denser and heavier than the microvessel endothelial cells. The method also preferably includes the further step of isolating the digested tissue in the form of a pellet of microvessel endothelial cells by selective application of the valves 37,45, as discussed above.

Figure 8:
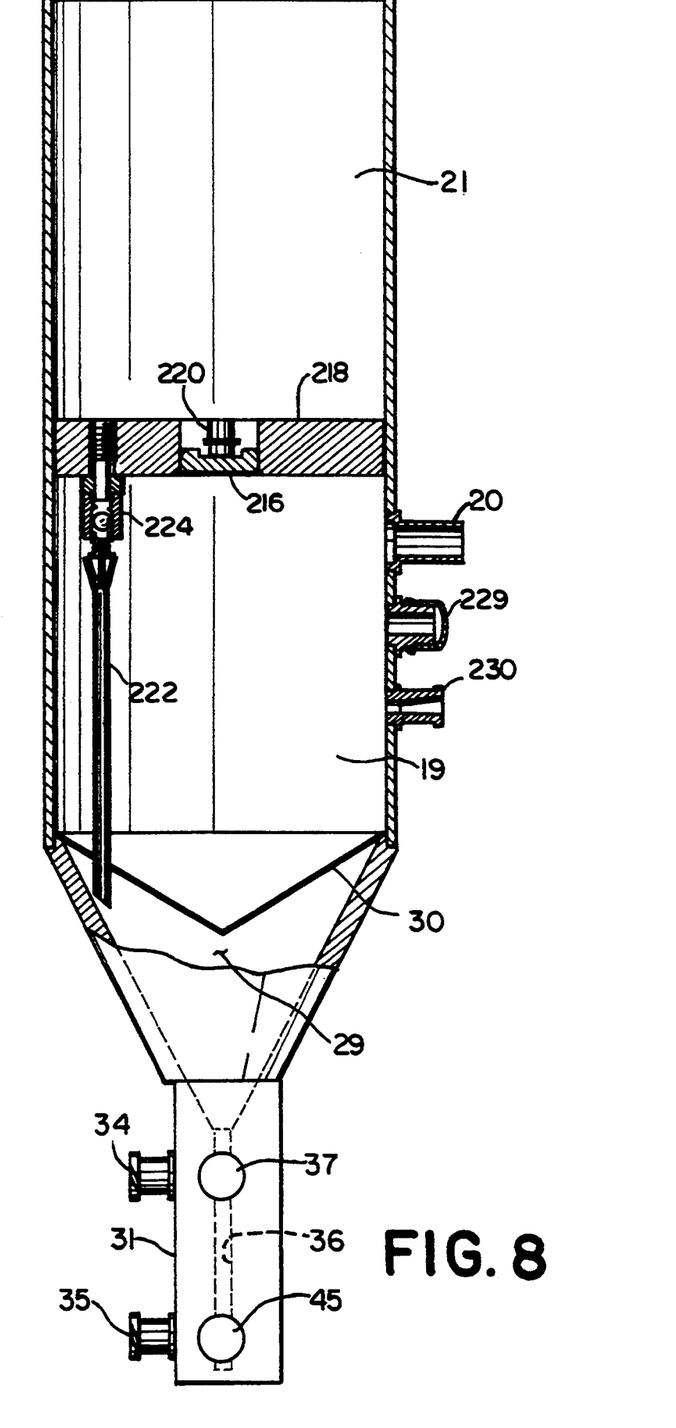
FIG. 8 is an enlarged longitudinal cross-section of another embodiment of a collection and processing device.

In accordance with the present invention, the fat collection and processing functions can also be performed in other embodiments of a single device, as shown in FIG. 8. As true for the embodiments shown in FIGS. 1–5, this embodiment is designed as a process vessel to collect, rinse and digest fat tissue and then separate and isolate microvessel endothelial cells for research, diagnostic or therapeutic purposes, e.g., endothelialization of a prosthetic or natural surface. The device has three chambers: a digestion chamber 19, a waste chamber 22, and an isolation chamber 29. The digestion chamber 19 is separated from the waste chamber 22 by a plate 218 containing a normally closed check valve 220. A vent tube 222, containing a floating ball check valve 224 extends from the waste chamber 22 into the isolation chamber 29. The digestion chamber 19 communicates with the outside by means of a series of ports 20,229,230. The digestion chamber 19 is separated from the isolation chamber 29 by a screen 30. The isolation chamber 29 possesses two ports 34,35, each of which contains a valve 37,45. The first position of each valve 37,45 allows communication between the middle of an ampule 36 formed between them. The second position of the valves 37,45 allows communication between the ampule 36 and the outside ports 34,35. When practicing the methods disclosed herein, it is preferred that both ampule valves 37,45 are initially in a first position, and the device shown in FIG. 8 is used as a catch-trap in line with a liposuction vacuum line connected to two of the ports 20,230 that connect to the digestion chamber 19. After fat is collected, the liposuction lines are disconnected and the ports 20,230 are capped. Rinse solution (e.g., Media 199E, Hanks, saline, PBS, or other physiological buffered solution) is introduced through another port 229. The fat is agitated in the rinse solution by any external means such as shaking on a shaker table, manual agitation, etc. Agitation may also be accomplished by using inlet 230 port or a similar port to admit gas to the sealed digestion chamber 19 to agitate the tissue. The device is then placed in a centrifuge, ampule side up, and spun until the normally closed check valve 220 opens and the rinse solution wastes into the waste chamber 22. The ball valve 224 in the vent tube 222 opens during this centrifugation step allowing the waste chamber 22 to vent any air which is displaced by the rinse solution. Digestive enzyme solution such as collagenase, dispase, trypsin, or other tissue dissociation enzyme is then introduced through the same port 229 as the rinse solution, again followed by agitation. When digestion is complete, the device is again centrifuged, ampule side down. In order to isolate the endothelial cells which have separated into the ampule 36, both valves 37,45 are turned to their second positions. An endothelial cell "pellet" is then flushed out by attaching a pressure line to one of the ampule ports 34,35.

Figure 9:
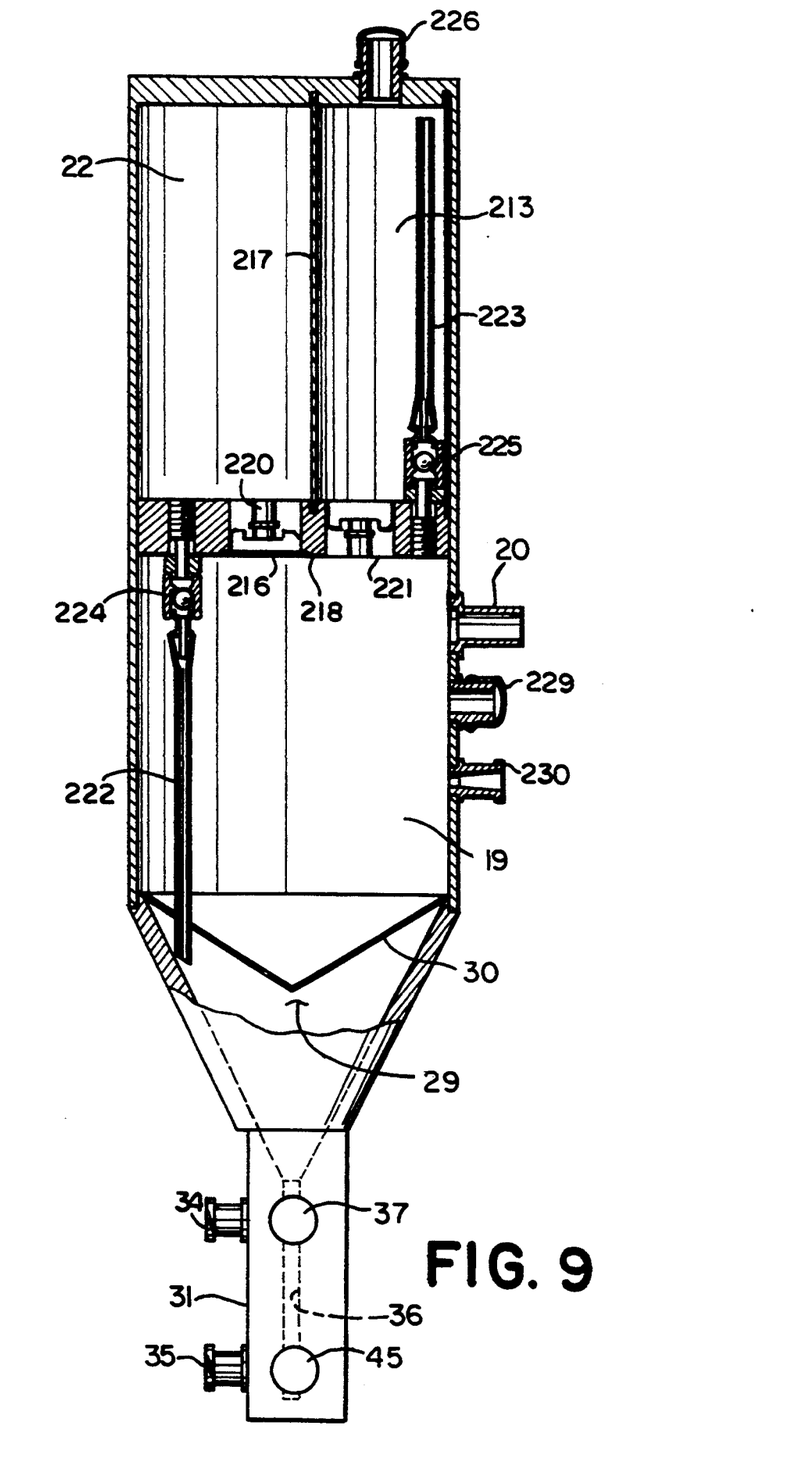
FIG. 9 is an enlarged longitudinal cross-section of another embodiment of the collection and processing device.

In another embodiment shown in FIG. 9 a device is provided that comprises a vessel with four chambers: a digestion chamber 19, a waste chamber 22, an enzyme chamber 213, and an isolation chamber 29. The digestion chamber 19 is separated from the waste chamber 22 by a plate 218 containing a normally closed check valve 220. A screen 216 covers the inlet of the check valve 220. A vent tube 222, containing a floating ball check valve 224, extends from the waste chamber 22 into the isolation chamber 29. The waste chamber is separated from the enzyme chamber by a plate 217. The digestion chamber 19 is separated from the enzyme chamber 213 by a plate 218 containing a normally closed check valve 221. A vent tube 223, containing a floating ball check valve 225 extends from the digestion chamber 19 into the top portion of the enzyme chamber 213. The enzyme chamber 213 communicates with the outside by means of a port 226. The digestion chamber 19 communicates with the outside by means of a series of ports 20,229,230. The digestion chamber 19 is separated from the isolation chamber 29 by a screen 30. The isolation chamber 29 possesses two ports 34,35, each of which contains a valve 37,45 that in their first position allow communication between the middle of the ampule 36 and the upper and lower portions of the ampule 36. The second position allows communication between the middle of the ampule 36 and the outside ports 34,35.

Initially, both valves 37,45 are in the first position. The device is used as a catch-trap in line with a liposuction line connected to two of the ports 20,230. After fat is collected, the liposuction lines are disconnected and ports 20,230 are capped. Rinse solution (e.g., Media 199E, Hanks, saline, PBS, or other physiological buffered solution) is introduced through port 229 and digestive enzyme solution (e.g., collagenase, dispase, trypsin, or other tissue dissociation enzyme) is introduced through port 226. The fat is agitated in the rinse solution by an external means such as shaking. The device is then placed in a centrifuge, ampule side up, and spun until the normally closed check valve 220 opens and the rinse solution drains into the waste chamber 22. The ball valve 224 in the vent tube 222 opens during this centrifugation step, allowing the waste chamber 22 to vent any air displaced by the rinse solution. The device is then placed in a centrifuge, ampule side down, and spun until the normally closed check valve 221 opens and enzyme solution drains into the digestion chamber 19. The ball valve 225 in the vent tube 223 opens during this centrifugation step allowing the digestion chamber 19 to vent air which is displaced by enzyme solution. The fat is then agitated in the enzyme solution to promote digestion. When digestion is complete, the device is again centrifuged, ampule side down. In order to isolate the endothelial cells which have separated into the ampule 36 both valves 37,45 are turned to their second positions. The endothelial cell pellet may then be flushed out by attaching a pressure line to one of the ampule ports 34,35.

While the forms of apparatus and the method described herein constitute preferred embodiments of the invention, it is to be understood that the invention is not limited to these preferred forms of apparatus and methods, and that changes can be made therein without departing from the inventive concepts disclosed herein. For example, various screen pore configurations may be developed to enhance separation. Moreover, centrifugal force control and agitation intensity may be varied to enhance output quantity and quality of the final cell pellet. In addition, the main digestion chamber, while shown in cylindrical form in cross-section, may be configured to be square for certain operating room accommodations. Therefore, reference should be made to the appended claims in order to ascertain the true scope of the present invention.

What is claimed is:

1. A method for collecting and processing tissue for producing an endothelial cell product comprising:
    providing a collecting vessel for processing tissue to produce an endothelial cell product, the vessel having a rinsing and digesting chamber in fluid communication with a separate waste chamber and an isolation chamber connected to the rinsing and digesting chamber, wherein a screen separates at least the rinsing and digesting chamber and the waste chamber;
    introducing tissue to be processed into the rinsing and digesting chamber;
    introducing rinsing solution into the rinsing and digesting chamber;
    orienting the vessel to screen the tissue to be processed of rinsing solution passed into the waste chamber;
    introducing an enzyme into the rinsing and digesting chamber;
    heating the tissue and the enzyme for a sufficient time and temperature while agitating the rinsing and digesting chamber to digest the tissue with the enzyme;
    centrifuging the vessel to transfer cells from the digested tissue from the rinsing and digesting chamber into the isolation chamber; and
    isolating the cells as a pellet of microvessel endothelial cells.

2. The method of claim 1 with the further step of isolating the cells from the digested tissue in an ampule as a pellet of microvessel endothelial cells by application of a valve means selectively connecting the isolation chamber and the ampule.

3. A device for digesting and processing tissue to produce an endothelial cell product comprising:
a single vessel comprising three chambers: a digestion chamber; a separate waste chamber; and a separate isolation chamber, said waste and isolation chambers in fluid communication with the digestion chamber, wherein the isolation chamber is selectively connected by a first valve to an ampule for receiving said endothelial cell product, and wherein the digestion chamber is selectively and alternately in fluid communication with the waste chamber and the isolation chamber,
whereby the device allows the digestion of tissue by connecting the digestion chamber to the waste chamber, and processing of tissue by connecting the digestion chamber to the isolation chamber to produce endothelial cell product within said single vessel under sterile conditions.

4. The device of claim 3 further comprising a normally closed check valve connecting the digestion chamber and the waste chamber.

5. The device of claim 4 further comprising an internal vent tube for permitting flow through the check valve, the vent tube extending from the waste chamber into the isolation chamber and a valve regulating fluid flow between the waste chamber and the isolation chamber.

6. The device of claim 3 further comprising a second valve, each of said first and second valves having at least two positions, wherein in its first position the first valve allows communication between the isolation chamber and the ampule, and when in its first position the second valve allows communication between the ampule and an outlet port, and wherein, in a second position the valves are closed to isolate endothelial cell product within the ampule.

7. The device of claim 3 further comprising at least one inlet port affixed to the vessel in communication with the digestion chamber for introducing collected fat, rinse and enzyme solutions into said digestion chamber.

8. A device for collecting and processing tissue to produce an endothelial cell product, comprising a vessel for rinsing, draining, digesting and isolating tissue the vessel comprising:
a rinsing and digesting chamber in the vessel for collecting and processing tissue;
an inlet connected to the rinsing and digesting chamber for receiving rinsing solution and also for receiving tissue from a liposuction means for withdrawing tissue from a subject;
a waste chamber in fluid communication with the rinsing and digesting chamber, the waste chamber further comprising a connection for fluid communication with a vacuum source;
a first screen separating the rinsing and digesting chamber from the waste chamber wherein waste fluid comprising rinsing solution flows from the rinsing and digesting chamber through the first screen to the waste chamber;
an isolation chamber in fluid communication with and separated from the rinsing and digesting chamber by a second screen to allow cells from rinsed, digested and processed tissue produced under sterile conditions to be isolated;
an ampule connected to and in selective fluid communication with said isolation chamber;
a pair of ports connected to the ampule, one of the ports providing a selective connection between the isolation chamber and the ampule and another of the ports providing selective communication between the ampule and an external environment; and
valve means operatively associated with each of the ports to selectively control fluid communication between each of the ports, the ampule, the external environment and the isolation chamber,
whereby endothelial cells disposed in the ampule are isolated by selective operation of the valve means.

9. A device for digesting and processing tissue to produce an endothelial cell product comprising:
a single vessel comprising four chambers: (a) an enzyme storage chamber; (b) a separate waste chamber; (c) a separate digestion chamber alternately and selectively connected to the waste chamber and the enzyme chamber; and (d) a separate isolation chamber selectively connected to the digestion chamber, wherein the isolation chamber is selectively connected by a first valve to an ampule for receiving said endothelial cell product, whereby the device allows the digestion of tissue by connecting the digestion chamber to the enzyme storage chamber and the waste chamber and processing of tissue by connecting the digestion chamber to the isolation chamber to produce endothelial cell product within a single vessel under sterile conditions.

10. The device of claim 9 wherein said enzyme storage chamber selectively communicates with said digestion chamber through a valve and said enzyme storage chamber communicates with an external environment through a port.

11. The device of claim 10 wherein the valve between said enzyme storage chamber and said digestion chamber is a normally closed check valve which opens when pressure increases inside said enzyme storage chamber upon centrifugation of said device.

12. The device of claim 9 wherein said digestion chamber further comprises a means to introduce tissue to be digested within said digestion chamber, and a means to introduce rinsing fluid into said digestion chamber for rinsing said tissue.

* * * * *